(12) United States Patent
Säll et al.

(10) Patent No.: US 11,110,223 B2
(45) Date of Patent: Sep. 7, 2021

(54) SUPPLEMENTARY DEVICE FOR A MEDICAMENT DELIVERY DEVICE

(71) Applicant: SHL MEDICAL AG, Zug (CH)

(72) Inventors: Daniel Säll, Segeltorp (SE); Anders Holmqvist, Värmdö (SE)

(73) Assignee: SHL MEDICAL AG, Zug (CH)

( * ) Notice: Subject to any disclaimer, the term of this patent is extended or adjusted under 35 U.S.C. 154(b) by 406 days.

(21) Appl. No.: 16/304,867

(22) PCT Filed: May 22, 2017

(86) PCT No.: PCT/EP2017/062260
§ 371 (c)(1),
(2) Date: Nov. 27, 2018

(87) PCT Pub. No.: WO2017/215887
PCT Pub. Date: Dec. 21, 2017

(65) Prior Publication Data
US 2020/0324050 A1    Oct. 15, 2020

(30) Foreign Application Priority Data

Jun. 16, 2016  (EP) .................................. 16174876

(51) Int. Cl.
*A61M 5/24* (2006.01)
*A61M 5/315* (2006.01)
(Continued)

(52) U.S. Cl.
CPC ............ *A61M 5/24* (2013.01); *A61M 5/2033* (2013.01); *A61M 5/3158* (2013.01);
(Continued)

(58) Field of Classification Search
CPC ............ A61M 5/2033; A61M 5/31571; A61M 5/3158; A61M 2005/14208;
(Continued)

(56) References Cited

U.S. PATENT DOCUMENTS

| 6,193,698 B1 | 2/2001 | Kirchhofer et al. |
| 2006/0089594 A1* | 4/2006 | Landau .................. A61M 5/30 604/68 |

(Continued)

FOREIGN PATENT DOCUMENTS

| CN | 102413852 A | 4/2012 |
| CN | 102413856 A | 4/2012 |

(Continued)

OTHER PUBLICATIONS

Chinese Office Action for CN Application No. 201780034844.X, dated Jul. 21, 2020.

(Continued)

*Primary Examiner* — Nathan R Price
*Assistant Examiner* — Tasnim Mehjabin Ahmed
(74) *Attorney, Agent, or Firm* — McDonnell Boehnen Hulbert & Berghoff LLP (57) ABSTRACT

The present disclosure relates to a supplementary device (1) configured to be mounted to a medicament delivery device (1), wherein the supplementary device comprises a casing (3), a button (5) configured to be received by the casing (3) and configured to actuate a trigger (6) of a medicament delivery device (2), wherein the button (5) is configured to be displaceable from an initial retracted position to an extended position relative to the casing (3), and a button locking member (7) configured to lock the button (5) in the retracted position of the button (5) to prevent displacement of the button (5) from the retracted position to the extended position, wherein the button locking member (7) is configured to release button (5) when the supplementary device (1) is mounted to a medicament delivery device (2), thereby enabling displacement of the button (5) from the retracted position to the extended position.

19 Claims, 9 Drawing Sheets

(51) Int. Cl.
  *A61M 5/20* (2006.01)
  *G16H 20/13* (2018.01)
  *G16H 20/17* (2018.01)

(52) U.S. Cl.
  CPC . *A61M 5/31571* (2013.01); *A61M 2005/2006* (2013.01); *A61M 2005/2073* (2013.01); *G16H 20/13* (2018.01); *G16H 20/17* (2018.01)

(58) Field of Classification Search
  CPC .. A61M 2005/2006; A61M 2005/2026; A61M 2005/2073; G01D 5/1655
  See application file for complete search history.

(56) References Cited

U.S. PATENT DOCUMENTS

2006/0224124 A1* 10/2006 Scherer ............... A61M 5/2033 604/220
2011/0313350 A1* 12/2011 Krulevitch ........ A61M 5/31525 604/65

FOREIGN PATENT DOCUMENTS

| | | |
|---|---|---|
| CN | 103458942 A | 12/2013 |
| CN | 103476444 A | 12/2013 |
| CN | 103648555 A | 3/2014 |
| CN | 104136058 A | 11/2014 |
| CN | 104203315 A | 12/2014 |
| JP | 2012-519026 A | 8/2012 |
| JP | 2014-516599 A | 7/2014 |
| JP | 2014-520583 A | 8/2014 |
| WO | 02/064196 A1 | 8/2002 |
| WO | 2007/107564 A1 | 9/2007 |
| WO | 2013/004843 A1 | 1/2013 |
| WO | 2013/004844 A1 | 1/2013 |
| WO | 2013/079429 A1 | 6/2013 |
| WO | 2015/028393 A1 | 3/2015 |

OTHER PUBLICATIONS

International Search Report and Written Opinion for Int. App. No. PCT/EP2017/062260, dated Aug. 18, 2017.

* cited by examiner

SUPPLEMENTARY DEVICE FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2017/062260 filed May 22, 2017, which claims priority to European Patent Application No. 16174876.9 filed Jun. 16, 2016. The entire disclosure contents of these applications are herewith incorporated by reference into the present application.

TECHNICAL FIELD

The present disclosure generally relates to medical devices. In particular, it relates to a supplementary device for a medicament delivery device.

BACKGROUND

Modern medicament delivery devices, such as auto-injectors, are designed to facilitate medicament administration in a manner which allows users to administer medicaments themselves. This freedom for patients to handle medicament delivery has lead to the concept of adherence, or compliance, to become an increasingly important area in treatment of illnesses. Adherence involves monitoring of a patient's medication administration scheme as prescribed by a physician and evaluation of whether a prescribed medicament and medicament administration scheme has been successful or not in treating the illness of the patient.

It has been found that it is relatively common that a user does not administer the medication as prescribed. Reasons for a patient's failure to comply with the prescribed scheme include forgetfulness, pain associated with drug administration or discomfort experienced from side effects of the medication.

Failure to comply with a drug administration scheme may result in that the patient can experience poor recovery from an illness, and it may furthermore result in secondary diseases requiring additional medical attention. This may in turn bring unnecessary pressure on the healthcare system.

In view of the above, it is in the interest of both patients' and the healthcare to facilitate monitoring to increase the occurrences of medicament administration as prescribed.

WO2007/107564 A1 discloses an electronic module for mechanical medication delivery devices, and aims at monitoring the operation of a medication delivery device. This document discloses an electronic module that is attached onto a medication delivery device. The electronic module is capable of measuring acoustical and/or vibrational signals generated in response to relative movements of internal parts of the medication delivery device to which the electronic module is attached. Such internal parts can be mechanical parts which during movement generate for example acoustical sounds, such as click sounds. The electronic module is powered by a built-in battery which powers the module when for example a capacitive touch pad is activated. This activation is performed when for example a finger tip is positioned on the touch pad.

In WO2007/107564 A1 the battery and thus the electronic module is activated provided a user touches the touch pad located on the electronic module. This touch pad is not associated with the mechanical operation of the medication delivery device. There is hence a risk that a user will forget to activate the electronic module prior to drug administration. This would result in that the following drug administration would not be registered.

SUMMARY

A general object of the present disclosure is to provide a supplementary device for a medicament delivery device which solves or at least mitigates the problems of the prior art.

There is hence according to a first aspect of the present disclosure provided a supplementary device configured to be mounted to a medicament delivery device, wherein the supplementary device comprises: a casing, a button configured to be received by the casing and configured to actuate a trigger of a medicament delivery device, wherein the button is configured to be displaceable from an initial retracted position to an extended position relative to the casing, and a button locking member configured to lock the button in the retracted position of the button to prevent displacement of the button from the retracted position to the extended position, wherein the button locking member is configured to release the button when the supplementary device is mounted to a medicament delivery device, thereby enabling displacement of the button from the retracted position to the extended position.

Users are thereby prevented from actuating the button until the supplementary device is mounted to a medicament delivery device. In particular, the button is unlocked by the outer geometry of a medicament delivery device.

According to one embodiment the button locking member comprises a radially flexible arm configured to engage with the button to prevent displacement of the button from the retracted position to the extended position.

According to one embodiment the button has a radial flange having a first surface, and wherein the radially flexible arm has a distal end configured to bear against the first surface to prevent the button from displacement from the retracted position to the extended position.

According to one embodiment the radially flexible arm is configured to bear against the first surface of the radial flange in a radially unbiased state of the radially flexible arm.

According to one embodiment the radially flexible arm is configured to be bent radially outwards to disengage from the first surface of the radial flange when the supplementary device is mounted to a medicament delivery device.

According to one embodiment the button locking member is configured to prevent displacement of the button from the extended position to the retracted position.

According to one embodiment the radial flange has a second surface opposite to the first surface configured to engage with the radially flexible arm when the button is in the extended position and the supplementary device is removed from the medicament delivery device to prevent displacement of the button from the extended position to the retracted position.

One embodiment comprises an electronics module and a first switch configured to activate the electronics module, wherein the first switch is configured to be actuated to activate the electronics module by displacement of the button from the retracted position to the extended position.

According to one embodiment the electronics module is configured to be mounted to an underside of the button, and wherein the first switch is configured to be mounted to the electronics module.

According to one embodiment the casing defines a tapering distal inner space, wherein the first switch is configured to contact an inner wall forming part of the tapering distal inner space of the casing when the button is displaced from the retracted position to the extended position, thereby activating the electronics module.

It may thereby be ensured that the electronics module is only activated once the supplementary device has been fitted to a medicament delivery device, by distal movement of the button.

According to one embodiment the button locking member is configured to be fixedly mounted to the casing.

According to one embodiment the button and the button locking member have cooperating guide structures configured to allow linear displacement of the button relative to the button locking member and to prevent relative rotation between the button and the button locking member.

One embodiment comprises an elongated protrusion extending axially in the proximal direction from below the button, which elongated protrusion is configured to actuate a trigger of a medicament delivery device.

One embodiment comprises a resilient member configured to bias the button towards the extended position, and a second switch configured to detect mechanical contact with a trigger of a medicament delivery device.

There is according to a second aspect of the present disclosure provided a medicament delivery device comprising: a housing, a trigger configured to extended at a distal end of the housing, and a supplementary device according to the first aspect, configured to be mounted to a distal end of the housing to enable actuation of the trigger by means of the button of the supplementary device, wherein the button locking mechanism is configured to be flexed radially by the housing or the trigger to release the button of the supplementary device.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc., unless explicitly stated otherwise.

BRIEF DESCRIPTION OF THE DRAWINGS

The specific embodiments of the inventive concept will now be described, by way of example, with reference to the accompanying drawings, in which:

FIG. 6B is a perspective view of an example of a medicament delivery device for use with the supplementary device shown in FIG. 6a;

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

The term "proximal end" as used herein, when used in conjunction with a supplementary device, refers to that end of the supplementary device which when assembled with a medicament delivery device is configured to receive the distal end of a medicament delivery device. The proximal end of the medicament delivery device is that end which is to be pointed towards the site of injection during a medicament expulsion. The "distal end" is the opposite end relative to the proximal end. The same considerations also apply when referring to any component of the supplementary device. With "proximal direction" and, equivalently, "proximally" is meant a direction from the distal end towards the proximal end, along the central axis of the cap assembly. With "distal direction" or "distally" is meant the opposite direction to "proximal direction".

The present disclosure relates to a supplementary device for a medicament delivery device, such as a disposable or multi-use medicament delivery device, e.g. a disposable auto-injector or a multi-use auto-injector. The supplementary device has a casing, a displaceable button, and a button locking member.

The supplementary device is configured to be mounted to a medicament delivery device. The supplementary device may be configured to be mounted coaxially with the medicament delivery device, at a distal end thereof. The button of the supplementary device is configured to enable activation of the medicament delivery device when mounted thereto. To this end, the button is configured to cooperate with a trigger of a medicament delivery device, such that linear displacement of button causes activating of the medicament delivery device. The button is initially, i.e. before being mounted to a medicament delivery device, configured to be prevented by the button locking member from movement from a retracted position to an extended position. The button is configured to be released when the supplementary device is mounted to a medicament delivery device. In particular, the button locking member is configured to cooperate with the outer geometry of the medicament delivery device when the supplementary device is mounted to a medicament delivery device, thereby releasing the button from its locked state.

Figure 1:
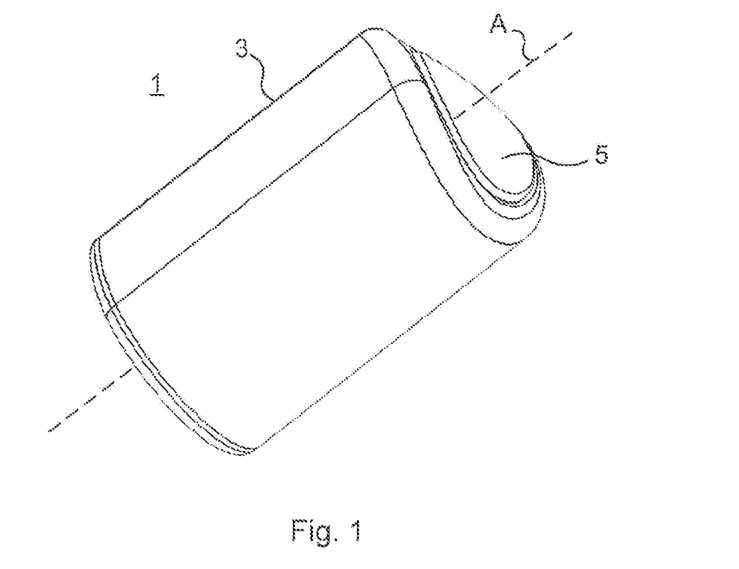
FIG. 1 is a perspective view of an example of a supplementary device for a medicament delivery device.

With reference to FIG. 1, an example of a supplementary device is shown. Supplementary device 1 has a hollow casing 3 provided with a through-opening extending parallel with the longitudinal axis A of the supplementary device 1. The supplementary device 1 furthermore has a button 5 received in the through-opening of the casing 3. The button 5 is manoeuvrable between a retracted position relative to the casing 3, shown in FIG. 1, and an extended position relative to the casing 3. The button 5 is initially configured to be locked in the retracted position, i.e. before being mounted to a medicament delivery device. The supplementary device 1 is designed to cooperate with the distal end of a medicament delivery device, such that when the supplementary device 1 is mounted to a medicament delivery device the button 5 is displaced from the retracted position to the extended position.

Figure 2:
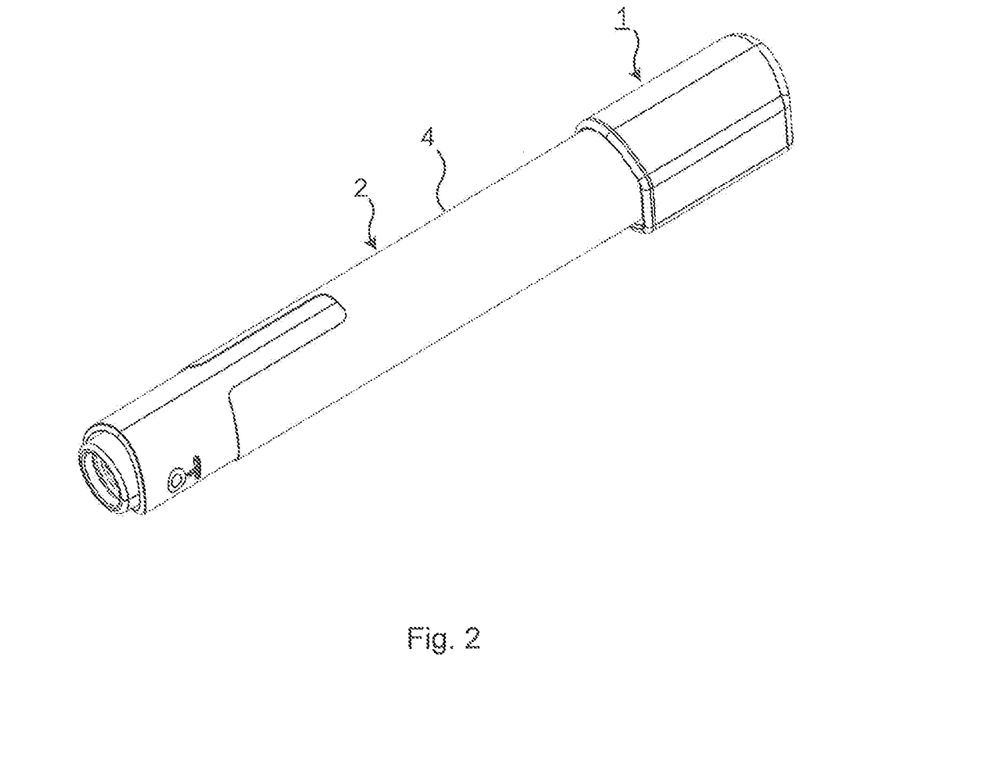
FIG. 2 is a perspective view of an example of a medicament delivery device having the supplementary device in FIG. 1 mounted thereto.

Turning to FIG. 2 an example of a medicament delivery device 2 having a body 4 is shown, with the supplementary device 1 being mounted to a distal end of the body 4.

Figure 3:
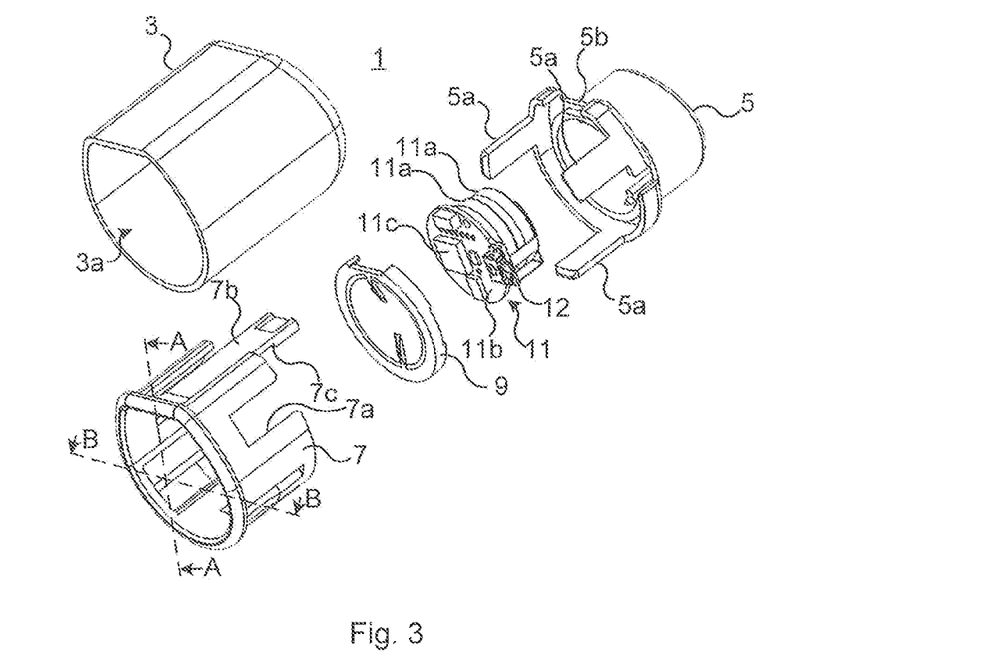
FIG. 3 is an exploded view of the supplementary device in FIG. 1.

FIG. 3 shows an exploded view of the supplementary device 1. In this figure, it can better be seen that the casing 3 has a through-opening 3a extending in the longitudinal direction of the supplementary device 1. The casing 3 is configured to displaceably receive the button 5.

The supplementary device 1 further comprises a button locking member 7. The button locking member 7 is configured to be received by the casing 3, in particular by the through-opening 3a. The button locking member 7 may be configured to extend along the inner surface of the casing 3. The button locking member 7 may hence have an essentially cylindrical shape, configured to receive a distal end of a medicament delivery device 2. The button locking member 7 is configured to be arranged in a fixed manner in the casing 3. The button locking member 7 is furthermore fixedly arranged relative to the button 5.

The button locking member 7 has guide structures 7a extending in the longitudinal direction and the button 5 has corresponding guide structures 5a extending in the longitudinal direction. The guide structures 7a and 5a are configured to cooperate, to allow linear displacement of the button 5 relative to the button locking member 7 and to prevent rotation of the button 5 relative to the button locking member 7. Moreover, the guide structures 7a and 5a are configured to restrict the amount of displacement of the button 5 in the proximal direction. Hereto, the guide structures 7a and 5a define the maximal retraction possibly of the button 5 relative to the casing 3.

According to the present example, the guide structures 5a of the button 5 and the button locking member 7 are distributed in the circumferential direction. The guide structures 5a are exemplified by three legs. The guide structures 5a of the button 5 could however be less or more in number than three; there could for example be two guide structures e.g. legs, or more than three guide structures e.g. legs. The guide structures 7a of the button locking member 7 may for example be in the form of a number of longitudinal cut-outs or recesses configured to receive respective guide structures 5a, or legs, allowing the guide structures 5a of the button 5 to run in the guide structures 7a of the button locking member 7.

As an alternative to the above configuration, the guide structures of the button could instead be cut-outs or recesses and the guide structures of the button locking member could be legs.

The button 5 furthermore has a radial flange 5b having a first surface 5c that forms a distal radial surface of the radial flange 5b and a second surface 5d opposite to the first surface, which second surface forms a proximal radial surface of the radial flange 5b. The button locking member 7 has a radially flexible arm 7b extending parallel with the longitudinal axis of the supplementary device 1. The radially flexible arm 7b is configured to be radially spaced apart from the inner wall of the casing 3 in a default radially unbiased state. Hereto, the radially flexible arm 7b may include a radially inwards extending portion 7d, shown in FIG. 4a, spacing the radially flexible arm 7b apart from the inner wall of the casing 3 when the button locking member 7 is arranged in the casing 3.

The radially flexible arm 7b is configured to engage with the button 5 when the button 5 is in or essentially in the retracted position. In particular, the radially flexible arm 7b has a blocking surface which is configured to block the radial flange 5b and bear against the first surface of the radial flange 5b when the button 5 is subjected to a force trying to push it from the retracted position towards the extended position, as long as the radially flexible arm 7b is not forced radially outwards to thereby disengage from engagement with the radial flange 5b. The radially flexible arm 7b may have a latch 7c which bears against the first surface of the button 5 to thereby prevent the button 5 from displacement from the retracted position to the extended position. When the supplementary device 1 is mounted to the distal end of a body of a medicament delivery device 2, the radially flexible arm 7b is bent outwards by the geometry of the body, thereby releasing the button 5 from being locked in the retracted position. The button 5 can thereby be pushed to the extended position by the trigger of the medicament delivery device while the supplementary device 1 is placed onto the medicament delivery device 2.

The supplementary member 1 furthermore has a pusher lid 9 and an electronics module 11 both configured to be received by the casing 3, and a first switch 12 configured to be mounted to the electronics module 11. The electronics module 11 is configured to be fixedly arranged relative to the button 5. Furthermore, the electronics module 11 is configured to be arranged proximally relative to the button 5. The electronics module 11 is thus configured to be arranged below the button 5. The button 5 may according to one variation have a space configured to receive the electronics module 11.

The electronics module 11 includes an energy storage device 11a e.g. one or more batteries and a circuit board 11b, processing circuitry 11c mounted on the circuit board 11b and a first switch 12. The first switch 12 is configured to activate the electronics module 11, for example to enable the energy storage device 11a to feed power to the processing circuitry 11c. The first switch 12 may also be configured to initiate timestamp generation of an injection, e.g. by triggering the processing circuitry 11c.

The electronics module 11 may furthermore optionally comprise an antenna configured to transmit data such as timestamp data obtained from the processing circuitry 11c for e.g. compliance/adherence purposes and/or a tactile, e.g. a vibrator, or visual indicator providing the user with feedback or information regarding correct use of the medicament delivery device to which the supplementary device is mounted, for example.

The electronics module 11 may according to one variation also include at least one of a microphone and a vibration sensor configured to detect characteristic vibrations of a medicament administration procedure of the medicament delivery device which it is to be used with.

The pusher lid 9 is configured to protect the electronics module 11 and to cooperate with a distal end of a medicament delivery device. The pusher lid 9 is arranged proximally relative to the electronics module 11.

Figure 4A:
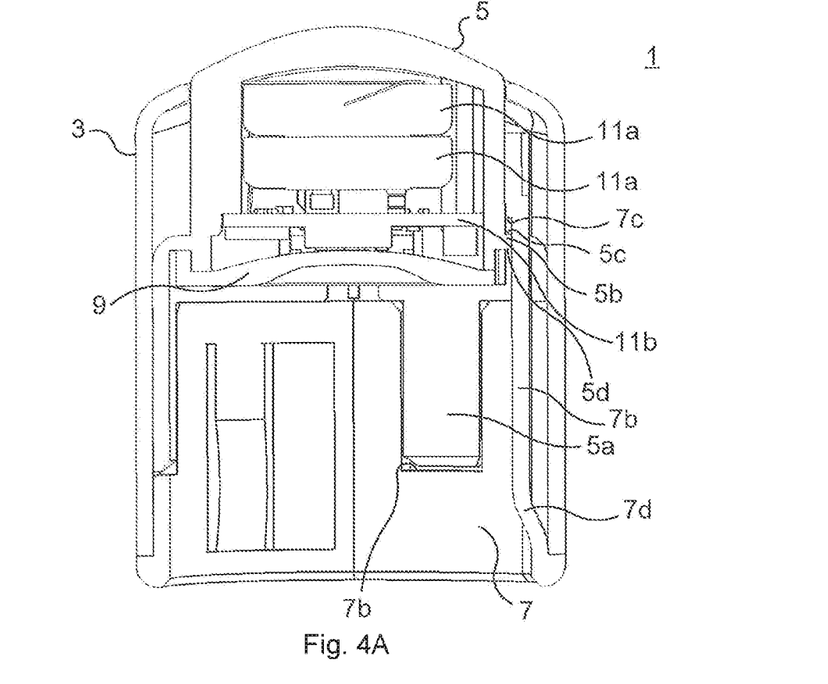
FIG. 4A is a longitudinal section of the supplementary device in FIG. 1.

Turning now to FIG. 4a a longitudinal section of the supplementary member 1 is shown. The longitudinal section is taken along lines A-A in FIG. 3. According to FIG. 4a the button 5 is in the retracted position relative to the casing 3. The radially flexible arm 7b extends beyond the radial flange 5b in the distal direction. The latch 7c, which defines a radial surface, is configured to limit linear displacement of the button 5 in the distal direction when the button 5 is in the retracted position.

Figure 4B:
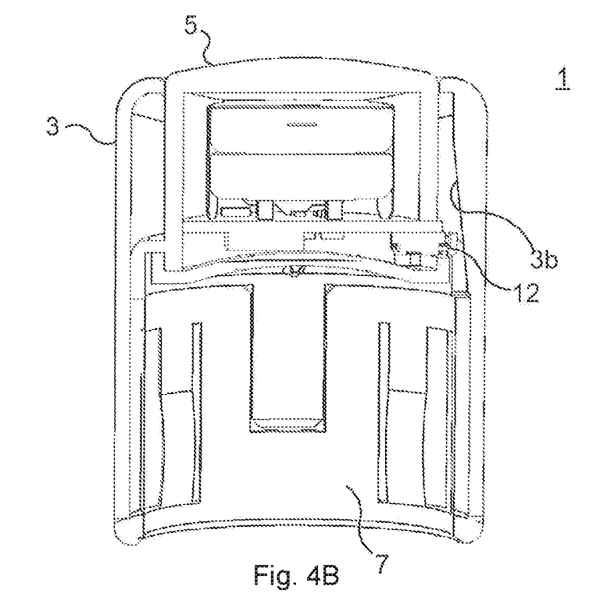
FIG. 4B is a longitudinal section of the supplementary device in FIG. 1 at 90 degrees angle with the longitudinal section shown in FIG. 4A.

In FIG. 4b, the supplementary device 1 is shown in a longitudinal section along lines B-B in FIG. 3, i.e. at a 90 degree angle relative to the longitudinal section shown in FIG. 4a. The button 5 is in the retracted position relative to the casing 3. The casing 3 has a distal portion which has an inner wall 3b that is inclined and defines an inner space in the casing 3. The inner space is tapering in the distal direction.

In the retracted position of the button 5, the first switch 12 is configured to be radially spaced apart from the inner wall 3b. When the button 5 has been released from its locked state by being mounted to a medicament delivery device, the first switch 12 is moved distally concurrently with the button 5, eventually contacting the inner surface 3b. The first switch 12 is thereby actuated, whereby the electronics module 11 is activated.

The mounting procedure of the supplementary device 1 to a medicament delivery device 2 will now be described with reference to FIGS. 5a-5d.

Figure 5A:
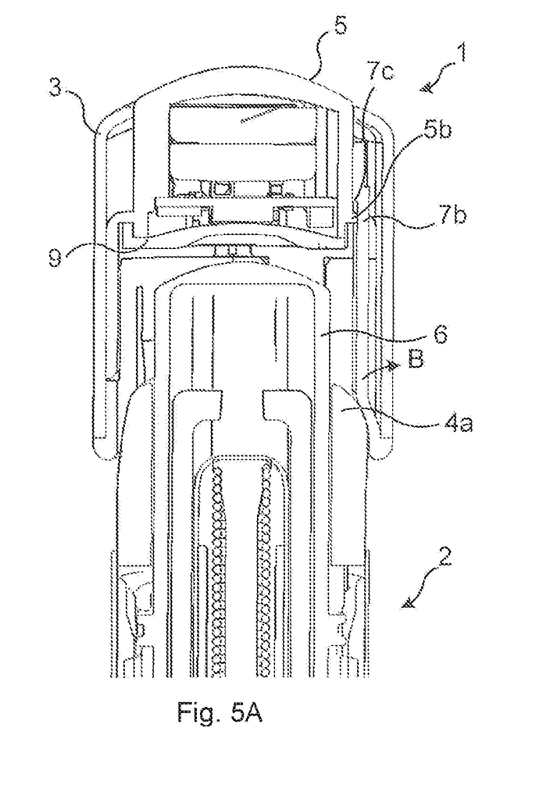
FIG. 5A shows a longitudinal section of the medicament delivery device in FIG. 2 including the supplementary device in various stages of operation.

The medicament delivery device 2 has a distal end portion 4a forming part of the body of the medicament delivery device 2. The medicament delivery device 2 furthermore includes a trigger, or activation button, 6 which by linear displacement from an extended position to a retracted position relative to the distal end portion 4a activates medicament administration. This functionality of medicament delivery devices is well-known in the art and will not be disclosed in any further detail herein.

In FIG. 5a, the supplementary device 1 is in the process of being assembled with the medicament delivery device 2. The trigger 6 and a portion of the distal end portion 4a have been received by the casing 3, but the trigger 6 has not yet reached the pusher lid 9. According to the exemplified embodiment, the distal end portion 4a bears against the radial flexible arm 7b, causing it to gradually flex radially outwards as the supplementary device 1 further receives the medicament delivery device 2, as shown by arrow B. However, at the stage shown in FIG. 5a, the radially flexible arm 7b still extends distally beyond the radial flange 5a of the button, with the latch extending radially inwards beyond the radial flange 5a, thus preventing the button 5 from displacement from the retracted position to the extended position.

Figure 5B:
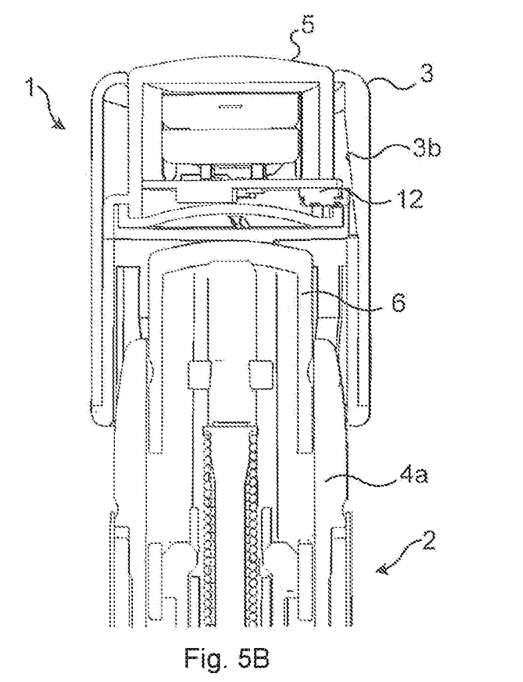
FIG. 5B shows a longitudinal section of the medicament delivery device in FIG. 2 including the supplementary device in various stages of operation.

FIG. 5b shows a different longitudinal section than FIG. 5a, namely along lines B-B in FIG. 3, in the same stage of the mounting procedure as FIG. 5a. It can be seen that the first switch 12 is arranged spaced apart from the inner wall 3b of the casing 3.

Figure 5C:
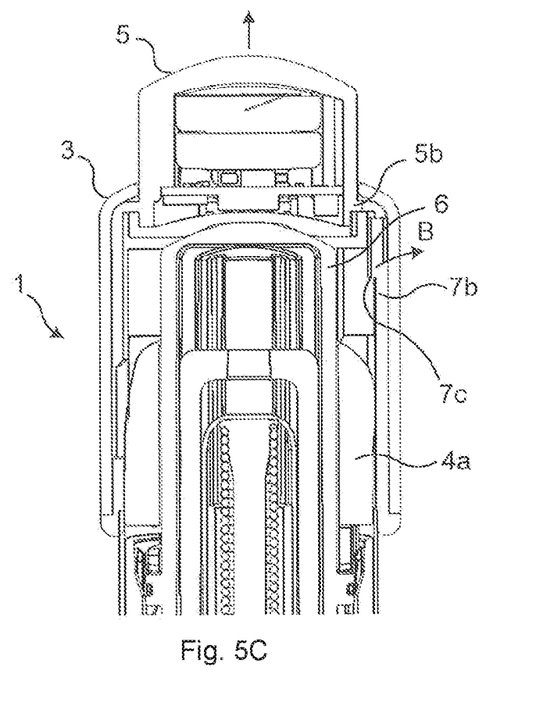
FIG. 5C shows a longitudinal section of the medicament delivery device in FIG. 2 including the supplementary device in various stages of operation.

FIG. 5c shows when the mounting stage has been completed. The supplementary device 1 has received a greater portion of the distal end of the medicament delivery device 2. Here, the distal end portion 4a has been fully received by the casing 3, and the radially flexible arm 7b has been flexed radially outwards by the distal end portion 4a, as illustrated by arrow B. The latch 7c has hence disengaged from, or been moved radially outwards from the radial flange 5a, and the button 5 has thereby been able to move distally from the retracted position to the extended position relative to the casing 3. This movement has been created because the force which biases the trigger 6 distally is greater than what is necessary to mount the supplementary device 1 to the medicament delivery device 2, and thus the trigger 6 is maintained in its initial position during the entire mounting procedure.

Figure 5D:
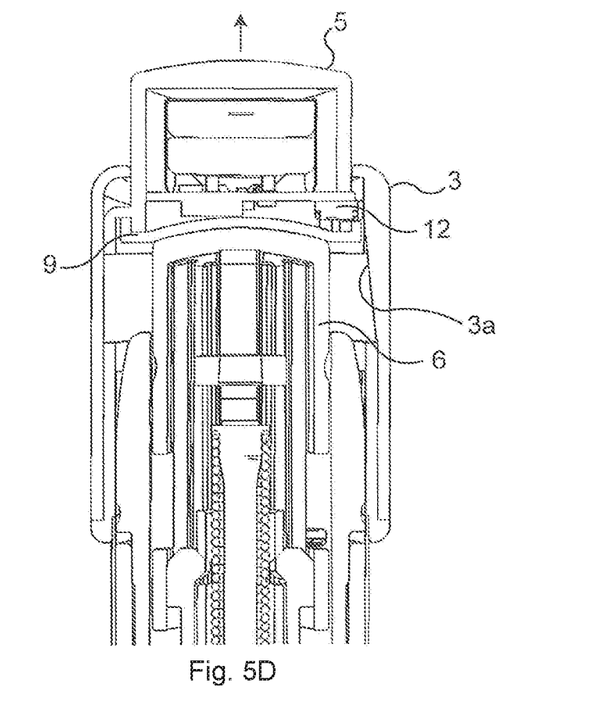
FIG. 5D shows a longitudinal section of the medicament delivery device in FIG. 2 including the supplementary device in various stages of operation.

FIG. 5d also depicts the completed mounting stage shown in FIG. 5c, but along the same longitudinal section as shown in FIG. 5b. As the button 5 has been displaced from the retracted position to the extended position, the first switch 12 has been moved radially closer to the inner wall 3b until making contact with the inner wall 3b. The first switch 12, which acts as a power switch, is thereby actuated activating the electronic components mounted on the circuit board 11b, such as processing circuitry 11c. The first switch 12 is hence in a sense configured to detect that the supplementary device 1 is mounted to the medicament delivery device 2.

When the supplementary device 1 has been mounted to the medicament delivery device 2, these two components may be seen to form a medicament delivery device with the added functionality of the supplementary device 1. The medicament delivery device 2 is thus ready for use, and the trigger 6 can be actuated by pressing the button 5 in the proximal direction, i.e. from the extended position towards its retracted position.

Figure 5E:
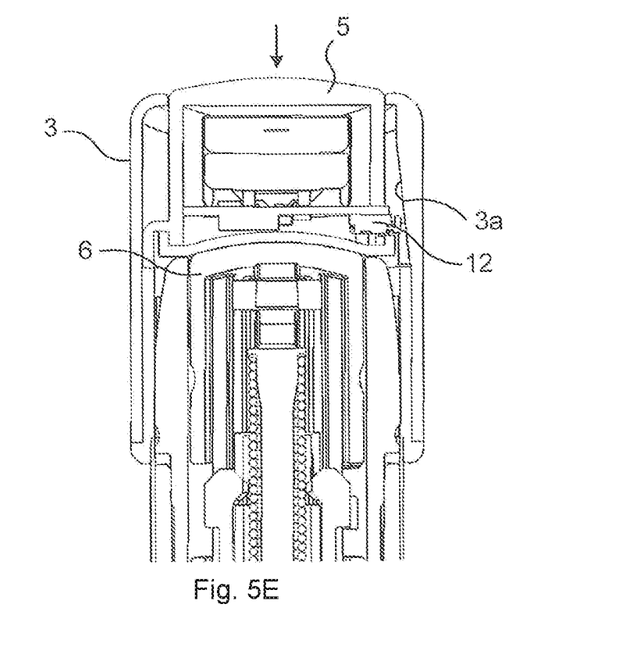
FIG. 5E shows a longitudinal sections of the medicament delivery device in FIG. 2 including the supplementary device in various stages of operation.

FIG. 5e depicts the same longitudinal section as shown in FIG. 5d, after triggering medicament administration i.e. when the button 5 has been pushed back to the retracted position thus displacing the trigger 6 proximally. The first switch 12 will in this case move again closer to the inner wall 3b until it contacts the inner wall 3b. This second contact between the first switch 12 the inner wall 3b again actuates the first switch 12, for example causing the processing circuitry 11c to generate a timestamp of an injection and to e.g. de-activate the electronic components on the circuit board 11b. In case a timestamp of the injection is generated when the first switch 12 contacts the inner wall 3b the antenna may be configured to transmit this timestamp to a remote device such as a mobile device, e.g. a smart phone or a tablet computer, which may be provided with a suitable application to process data transmitted from the supplementary device 1.

In case the button 5 for some reason is not actuated, i.e. pressed into the casing 3 to the retracted position, and the supplementary device 1 is removed from the medicament delivery device 2 when the button 5 is in the extended position, the radially flexible arm 7b will lock the button 5 in the extended position. In particular, the distal end of the radially flexible arm 7b will flex radially inwards upon removal of the supplementary device 1, moving in below the second surface of the radial flange 5a, i.e. proximally relative to the radial flange 5a, preventing the button 5 from being displaced from the extended position to the retracted position. The first switch 12 will hence in this case be prevented from being actuated a second time.

Figure 6A:
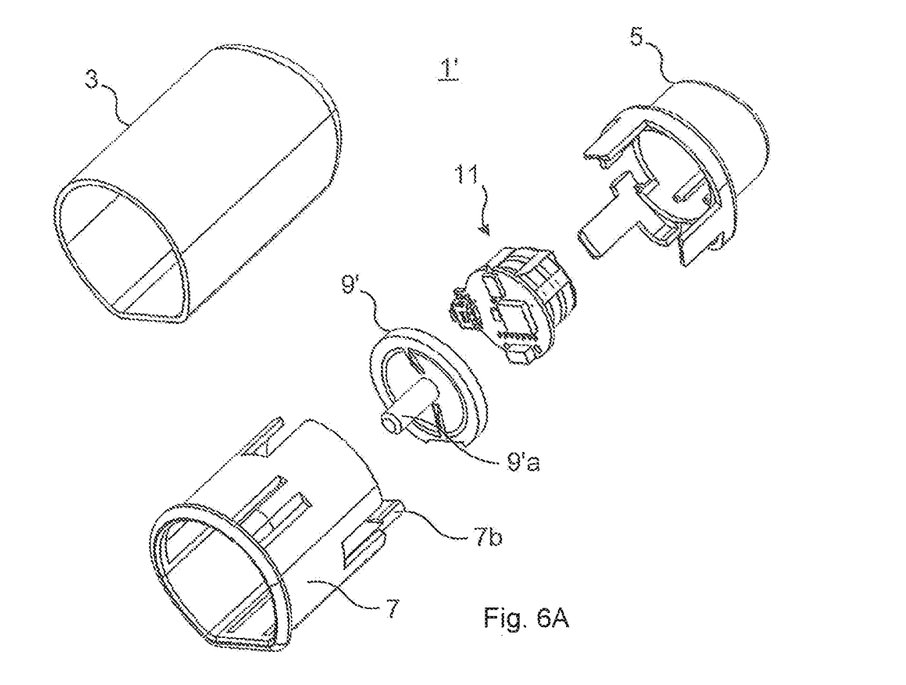
FIG. 6A is an exploded view of another example of a supplementary device.

FIG. 6a shows another variation of the supplementary device. Supplementary device 1' is very similar to the supplementary device 1 previously described. A difference between the supplementary device 1' and supplementary device 1 is that supplementary device 1' has a different type of pusher lid 9'. The pusher lid 9' has an elongated protrusion or rod 9'a extending axially in the proximal direction from an underside, i.e. a proximal side, of the pusher lid 9'. The elongated protrusion 9'a extends coaxially with the central axis of the supplementary device 1. The elongated protrusion 9'a is configured to actuate a trigger of a medicament delivery device 2', shown in FIG. 6b.

Figure 6B:
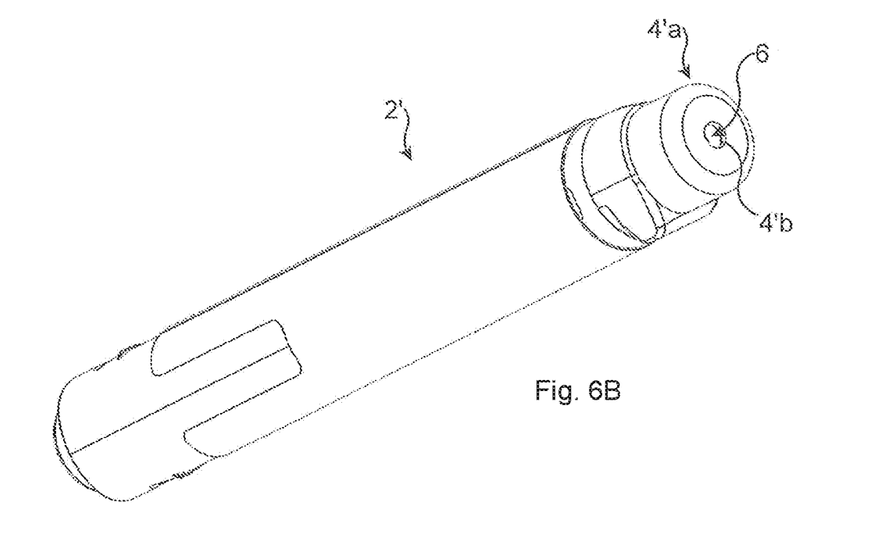

FIG. 6b depicts an example of a medicament delivery device 2' adapted for use with the supplementary device 1'. Medicament delivery device 2' is similar to medicament delivery device 2, but has a different distal end portion or rear end 4'a, which essentially encloses the trigger 6. The distal end portion 4'a has a through-opening 4'b extending coaxially with the longitudinal axis of the medicament delivery device 2', and which provides an opening to the trigger 6. The elongated protrusion 9'a is configured to be received by the through-opening 4'b to thereby actuate the trigger 6 when the button 5 is pushed from the extended position to the retracted position.

Figure 6C:
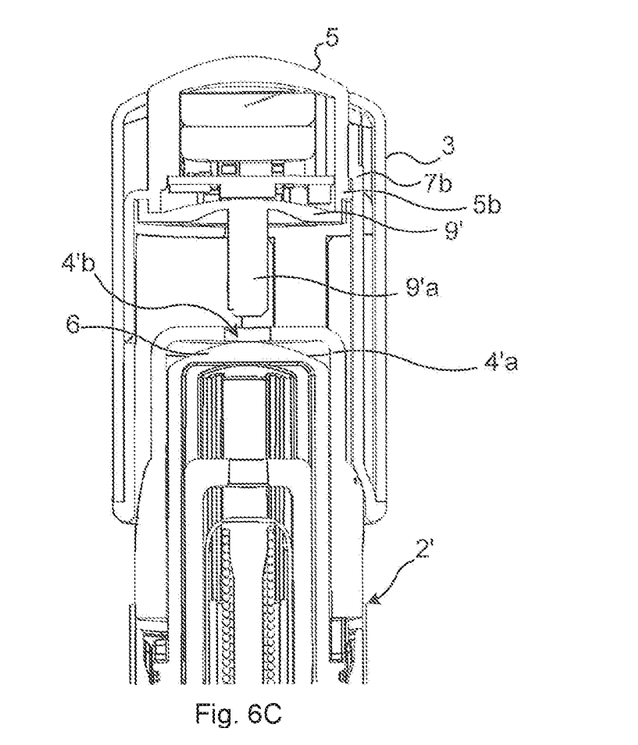
FIG. 6C is a longitudinal section of the supplementary device shown in FIG. 6a mounted to a medicament delivery device.

FIG. 6c shows the supplementary device 1' being mounted to the medicament delivery device 2'. The supplementary device 1' has not yet fully received the distal end portion 4'a and the radially flexible arm 7a has not yet been disengaged from the radial flange 5a. By applying the supplementary device 1' further onto the distal end portion 4'a, the radially flexible arm 7a will be flexed radially outwards as previously explained, and the button 5 will be allowed to move from the retracted position to the extended position relative to the casing 3.

In FIG. 6c, the elongated protrusion 9'a has not yet entered into the through-opening 4'b, but when it does and the supplementary device 1' is further pressed onto the medicament delivery device 2', the button 5 will be pushed from the retracted position to the extended position, and the medicament delivery device 2' will be ready for use.

By means of the elongated protrusion 9'a and the corresponding design of the distal end portion 4'a of the medicament delivery device 2' it can be ensured that activation of the medicament delivery device 2' is only possible with the supplementary device 1', unless the medicament delivery device 2' is manipulated with. This ensures that injection data, e.g. timestamps, created by the electronics module 11 will be generated for all injections.

Figure 7:
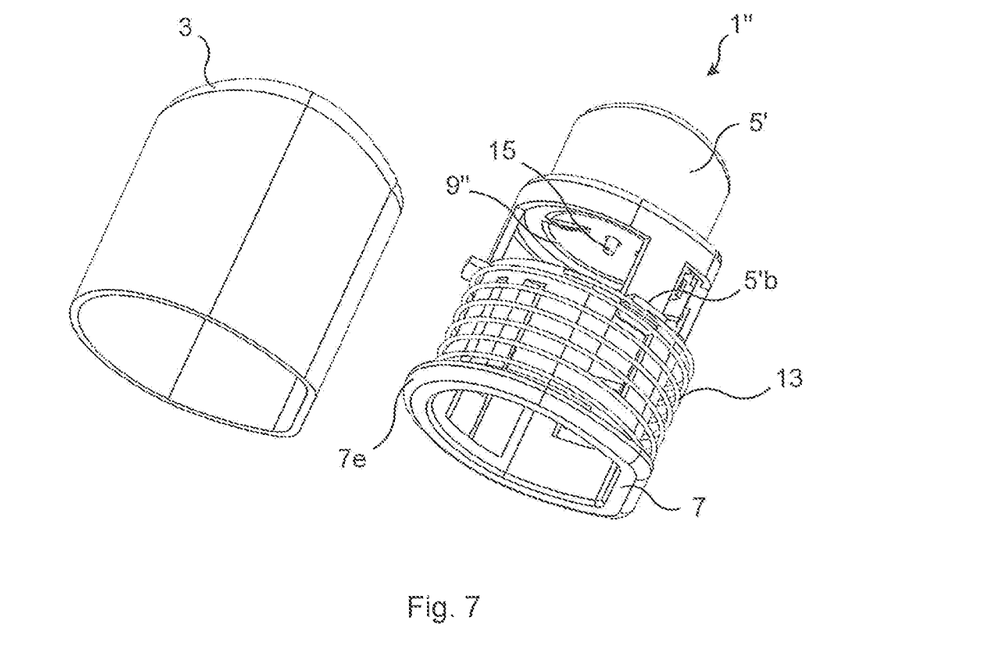
FIG. 7 is yet another example of a supplementary device for a medicament delivery device.

FIG. 7 shows yet another example of a supplementary device. Supplementary device 1" is similar to the supplementary device 1. Supplementary device 1" however furthermore includes a resilient member 13, such as a spring, configured to bias the button 5' distally towards the extended position. The button 5' will thereby return to the extended position after the button 5' has been pushed from the extended position to the retracted position when mounted to a medicament delivery device 2. Hereto, the button 5' may be provided with a plurality of radial protrusions 5'b and the button locking member 7 may have a proximal flange 7e and the resilient member 13 may be configured to be arranged between the radial protrusions 5'b and the proximal flange 7e, whereby the resilient member 13 biases the button 5' in the distal direction.

The supplementary device 1" furthermore has a pusher lid 9" provided with a second switch 15 arranged on the underside of the pusher lid 9", i.e. at a proximal side thereof. The second switch 15 is configured to detect contact with a distal end surface of the trigger 6 of the medicament delivery device 1. Without the second switch 15 the supplementary device 1" could be mounted to a used medicament delivery device which has a trigger, or activation button that is in a retracted position after use, and the geometry of the medicament delivery device could actuate the first switch and, depending on the implementation, trigger the generation of a timestamp of a medicament expulsion. However, with the second switch 15, it can be detected whether the medicament delivery device is previously unused, in which case the trigger 6 is in an extended position and will contact the second switch when the supplementary device 1" is mounted to a medicament delivery device, or if the supplementary device 1" is mounted to an used medicament delivery device, in which case no contact between the trigger 6 and the second switch 15 will be made. The second switch 15 hence facilitates for determining whether actuation of the first switch 12 is a result of the supplementary device 1" being mounted to an unused medicament delivery device 2 or not.

Figure 8A:
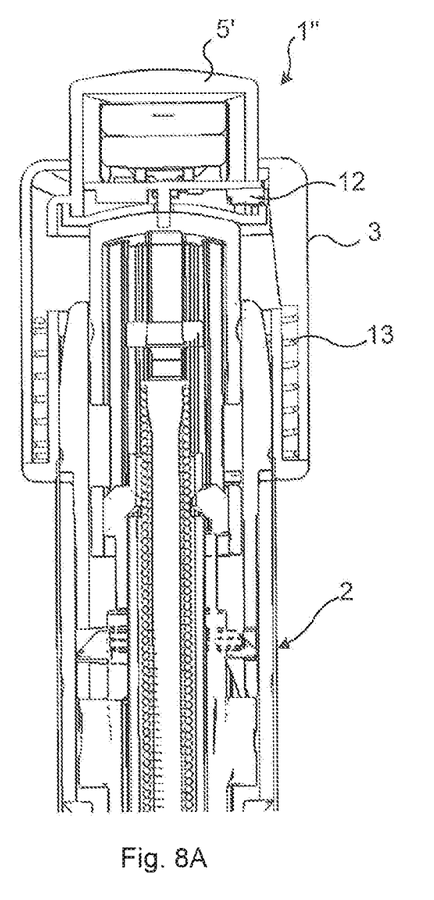
FIG. 8A shows the longitudinal section of the supplementary device in FIG. 7 mounted to a medicament delivery device in various stages of operation.
Figure 8B:
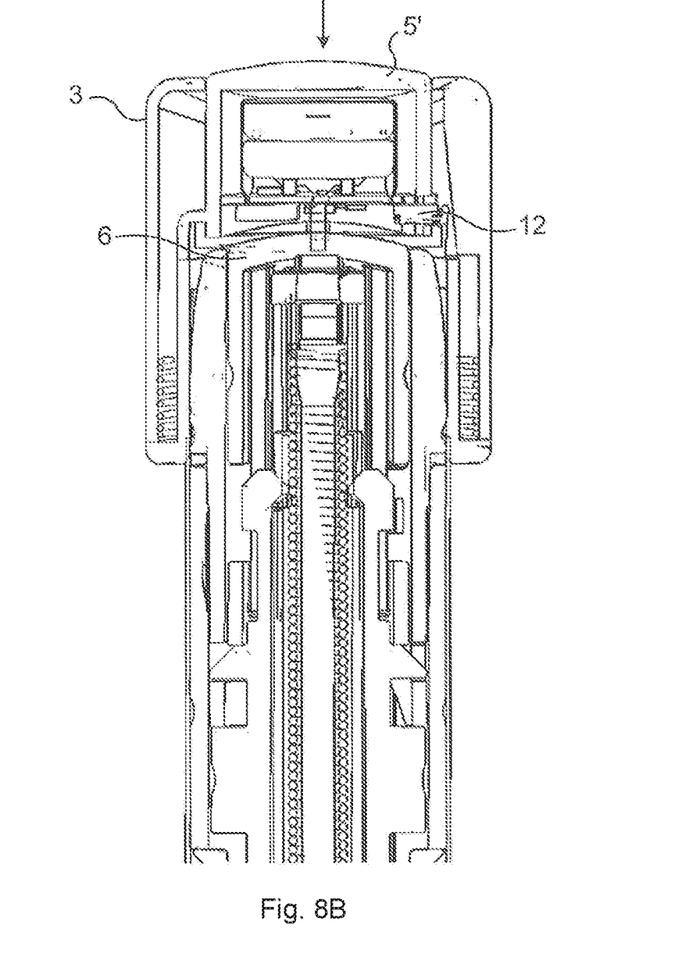
FIG. 8B shows the longitudinal sections of the supplementary device in FIG. 7 mounted to a medicament delivery device in various stages of operation.

FIG. 8a shows the supplementary device 1" mounted to a medicament delivery device 2 when the button 5' is set in the extended position and the medicament delivery device 2 is ready for use. FIG. 8b shows the supplementary device 1" after the button 5' has been pushed into the cover 3, to the retracted position, and thereby actuated the trigger 6.

As an alternative for any of the examples provided herein, the button locking member may be configured such that the outer geometry of the trigger of the medicament delivery device unlocks the button, instead of the outer geometry of the distal end portion of the medicament delivery device.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A supplementary device configured to be mounted to a medicament delivery device, wherein the supplementary device comprises:
   a casing,
   a button configured to be received by the casing and configured to actuate a trigger of the medicament delivery device, wherein the button is configured to be displaceable from an initial retracted position to an extended position relative to the casing, and
   a button locking member comprises a radial flexible arm that is configured to directly engage with and lock the button in the retracted position of the button to prevent displacement of the button from the retracted position to the extended position when the supplementary device is not mounted to the medicament delivery device,
   wherein the mounting of the supplementary device to the medicament delivery device disengages the flexible arm from the button such that the button is unlocked and released from the retracted position to allow displacement of the button to the extended position.

2. The supplementary device as claimed in claim 1, wherein the button has a radial flange having a first surface, and wherein the radially flexible arm has a distal end configured to bear against the first surface to prevent the button from displacement from the retracted position to the extended position.

3. The supplementary device as claimed in claim 2, wherein the radially flexible arm is configured to bear against the first surface of the radial flange in a radially unbiased state of the radially flexible arm.

4. The supplementary device as claimed in claim 3, wherein the radially flexible arm is configured to be bent radially outwards to disengage from the first surface of the radial flange when the supplementary device is mounted to the medicament delivery device.

5. The supplementary device as claimed in claim 2, wherein the button locking member is configured to prevent displacement of the button from the extended position to the retracted position.

6. The supplementary device as claimed in claim 5, wherein the radial flange has a second surface opposite to the first surface configured to engage with the radially flexible arm when the button is in the extended position and the supplementary device is removed from the medicament delivery device to prevent displacement of the button from the extended position to the retracted position.

7. The supplementary device as claimed in claim 1, comprising an electronics module having a first switch configured to activate the electronics module, wherein the first switch is configured to be actuated to activate the electronics module by displacement of the button from the retracted position to the extended position.

8. The supplementary device as claimed in claim 7, wherein the electronics module is configured to be mounted to an underside of the button, and wherein the first switch is configured to be mounted to the electronics module.

9. The supplementary device as claimed in claim 7, wherein the casing defines a tapering distal inner space, wherein the first switch is configured to contact an inner wall forming part of the tapering distal inner space of the casing when the button is displaced from the retracted position to the extended position, thereby activating the electronics module.

10. The supplementary device as claimed in claim 1, wherein the button locking member is configured to be fixedly mounted to the casing.

11. The supplementary device as claimed in claim 1, wherein the button and the button locking member have cooperating guide structures configured to allow linear displacement of the button relative to the button locking member and to prevent relative rotation between the button and the button locking member.

12. The supplementary device as claimed in claim 1, comprising an elongated protrusion extending axially in the proximal direction from below the button, which elongated protrusion is configured to actuate a trigger of the medicament delivery device.

13. The supplementary device as claimed in claim 1, comprising a resilient member configured to bias the button towards the extended position, and a second switch configured to detect mechanical contact with a trigger of the medicament delivery device.

14. A medicament delivery device comprising:
a housing,
a trigger configured to extended at a distal end of the housing, and
a supplementary device as claimed in claim 1, configured to be mounted to the distal end of the housing to enable actuation of the trigger by means of the button of the supplementary device,
wherein the button locking mechanism is configured to be flexed radially by the housing or the trigger to release the button of the supplementary device.

15. A supplementary device for attachment to a medicament delivery device, wherein the supplementary device comprises:
a casing,
a button movably positioned within the casing to move axially in a proximal direction from an initial retracted position to an extended position relative to the casing; and
a button lock comprising a radially flexible arm that is directly engaged with and releasably holds the button to maintain the button in the retracted position preventing displacement of the button from the retracted position to the extended position;
wherein the mounting of the supplementary device to the medicament delivery device disengages the flexible arm from the button such that the button is unlocked and released from the retracted position to allow displacement of the to the extended position, and
wherein the button has an interior portion comprising a battery operably connected to an electronics module through a switch.

16. The supplementary device of claim 15 wherein the button comprises a radial flange that is engaged with the radial flexible arm when the button is in the retracted position.

17. The supplementary device of claim 16 wherein the radial flexible arm is bent radially outward when the supplementary device is mounted to the medicament delivery device.

18. The supplementary device of claim 16 wherein the radial flexible arm engages the radial flange when the supplementary device is removed from the medicament delivery device preventing displacement of the button from the extended position to the retracted position.

19. The supplementary device of claim 15 wherein the button and the button lock have cooperating guide structures that prevent relative rotation between the button and the button lock.

* * * * *